United States Patent [19]

Kiener

[11] Patent Number: 5,273,893
[45] Date of Patent: Dec. 28, 1993

[54] MICROBIOLOGICAL PROCESS FOR THE PRODUCTION OF HYDROXYPYRAZINECARBOXYLIC ACID

[75] Inventor: Andreas Kiener, Visp, Switzerland

[73] Assignee: Lonza Ltd., Gampel/Valais, Switzerland

[21] Appl. No.: 894,009

[22] Filed: Jun. 4, 1992

[30] Foreign Application Priority Data

Jun. 21, 1991 [CH] Switzerland .................. 1843/91

[51] Int. Cl.$^5$ ........................ C12P 17/12; C12P 7/42
[52] U.S. Cl. ........................ 435/122; 435/146
[58] Field of Search ........................ 435/122, 146

[56] References Cited

U.S. PATENT DOCUMENTS

| | | | |
|---|---|---|---|
| 5,082,777 | 1/1992 | Lehky et al. | 435/122 |
| 5,213,975 | 5/1993 | Hoeks | 435/122 |
| 5,217,884 | 6/1993 | Zimmermann et al. | 435/122 |

FOREIGN PATENT DOCUMENTS

| | | | |
|---|---|---|---|
| 0152948 | 8/1985 | European Pat. Off. | 435/122 |
| 0434035 | 6/1991 | European Pat. Off. | 435/122 |

OTHER PUBLICATIONS

Tuntiwachwuttikul et al., J. Heterocyclic Chem., (1991), vol. 28, pp. 1331 to 1337.
Weiner et al., J. Pharmacol. Exp. Ther., (1972), vol. 180(2), pp. 411 to 434.
McCord et al., J. Heterocyclic Chem., vol. 19, (1982), pp. 401 to9 406.

*Primary Examiner*—Douglas W. Robinson
*Assistant Examiner*—Jeffrey J. Sevingny
*Attorney, Agent, or Firm*—Fisher, Christen & Sabol

[57] ABSTRACT

A microbiological process for the production of 5-hydroxypyrazinecarboxylic acid and/or its salts with microorganisms using nicotinic acid and/or its salts.

13 Claims, No Drawings

MICROBIOLOGICAL PROCESS FOR THE PRODUCTION OF HYDROXYPYRAZINECARBOXYLIC ACID

BACKGROUND OF THE INVENTION

1. Field of the Invention

The invention relates to a new process for the production of 5-hydroxypyrazinecarboxylic acid and/or its salts with nicotinic acid and/or its salts using microorganisms starting from pyrazinecarboxylic acid and/or its salts.

2. Background Art

In the following, by the term "nicotinic acid", "pyrazinecarboxylic acid" and "5-hydroxypyrazinecarboxylic acid" means the free acids as well as their salts, for example, their alkali salts or ammonium salts.

5-Hydroxypyrazinecarboxylic acid can be used, for example, as an intermediate product for the production of pharmaceutical agents, as well as, for example, for the production of pyrazine-nucleoside analogs having cytostatic effect P. Tuntiwachwuttikul, T. J. Bardos and M. Bobek, J. Heterocyclic Chem., (1991) Vol. 28, pages 1131 to 1137. It is known that 5-hydroxypyrazinecarboxylic acid in the metabolism of dogs and humans is formed from pyrazinamide via pyrazinecarboxylic acid [Weiner et al., J. Pharmacol. Exp. Ther., (1972), Vol. 180(2), 411–434 ].

A 5-stage chemical process for the production of 5-hydroxypyrazinecarboxylic acid has been described, for example, starting from furfuryl glyoxal [McCoral et al., J. Heterocyclic Chem., Vol. 19, (1982), page 402]. However, this process has the drawback that it is not feasible on an industrial scale.

So far no microbiological process for the production of 5-hydroxypyrazinecarboxylic acid is known.

BROAD DESCRIPTION OF THE INVENTION

The main object of the invention is to provide a simple economical and ecological process for the production of 5-hydroxypyrazinecarboxylic acid. Other objects and advantages of the invention are set out herein or obvious herefrom to one skilled in the art.

The objects and advantages of the invention are achieved by the process of the invention.

The invention involves a microbiological process for the production of 5-hydroxypyrazinecarboxylic acid and/or its salts. Pyrazinecarboxylic acid and/or its salts as substrate is converted with microorganisms, which grow with nicotinic acid and/or salts thereof as the sole carbon, nitrogen and energy source, into 5-hydroxypyrazinecarboxylic acid and/or salts thereof. The latter compound and/or salts accumulate in the medium.

Preferably the reaction is performed with microorganisms of genus Pseudomonas and/or Achromobacter and/or Bacillus and/or Azorhizobium and/or Sarcina and/or Mycobacterium. Preferably the reaction is performed with microorganisms of the species *Pseudomonas acidovorans* DSM 4746 or a descendant thereof or a mutant thereof. Preferably the reaction is performed with microorganisms of the species *Pseudomonas putida* NCIB 10521 or a descendant thereof or a mutant thereof. Preferably the reaction is performed with microorganisms of the species *Pseudomonas putida* NCIB 8176 or a descendant thereof or a mutant thereof. Preferably the reaction is performed with microorganisms of the species *Achromobacter xylosoxydans* DSM 2402 or a descendant thereof or a mutant thereof. Preferably the reaction is performed with microorganisms of the species *Achromobacter xylosoxydans* DSM 2783 or a descendant thereof or a mutant thereof. Preferably the reaction takes place under a single or continuous substrate addition, so that the substrate concentration does not exceed 20 percent. Preferably the reaction is performed under aerobic conditions at a pH of 4 to 10 and at a temperature of 10° to 60° C.

DETAILED DESCRIPTION OF THE INVENTION

According to the invention, pyrazinecarboxylic acid as substrate is converted with microorganisms, which grow with nicotinic acid as the sole carbon, nitrogen and energy source, into 5-hydroxypyrazinecarboxylic acid (or a salt thereof) and the latter accumulates in the medium.

In principle, all microorganisms which catabolize nicotinic acid by 6-hydroxynicotinic acid are suitable for the process. These microorganisms can be isolated with the help of usual microbiological techniques, for example, from sewage treatment plants with nicotinic acid as the growth substrate. For example, those microorganisms of the genus Pseudomonas, Achromobacter, Bacillus, Azorhizobium, Sarcina and Mycobacterium which are already described in U.S. Pat. No. 5,082,777 or European Published Patent Application No. 152948 as being used in the hydroxylation of nicotinic acid to 6-hydroxynicotinic acid, can be used in this invention. The pertinent portions of U.S. Pat. No. 5,082,777 are incorporated herein by reference. The reaction can be performed, sterile or nonsterile, with mixtures as well as with pure isolates of these microorganisms.

Suitably the process is performed with the microorganisms of the species *Pseudomonas acidovorans* DSM 4746, *Achromobacter xylosoxydans* DSM 2402, *Achromobacter xylosoxydans* DSM 2783, *Pseudomonas putida* NCIB 10521, and *Pseudomonas putida* NCIB 8176, as well as their descendants and mutants, preferably with *Pseudomonas acidovorans* DSM 4746. The microorganism of the species *Pseudomonas acidovorans* DSM 4746 was deposited on Jul. 25, 1988 in the Deutsche Sammlung von Mikroorganismen und Zellkulturen GmbH [German Collection for Microorganisms and Cell Cultures GmbH], Mascheroderweg 1b, D-3300 Brunswick, Germany. The microorganisms of the species *Achromobacter xylosoxydans* DSM 2402 and DSM 2783 have also been deposited in the above-mentioned institute and have already been described in U.S. Pat. No. 5,082,777 or European Published Patent Application No. 152948. The microorganisms of the species *Pseudomonas putida* NCIB 10521 and NCIB 8176 have been deposited in the National Collection of Industrial Bacteria, Torry Research Station, 135 Abbey Road, Aberdeen AB98DC, Scotland.

Taxonomic description of the strain *Achromobacter xylosoxydans* DSM 2783 is as follows: Isolated from: nicotinic acid mother lye

Morphology

Cultivation in Nutrient Broth (1) cell shape small rods 2 to 3.5 $\mu$ long, approximately 0.6 $\mu$ wide (2) arrangement: individually (3) motility: strongly movable; peritrically flagellated (4) endospore: none (5) gram: negative (6) oxidase: positive (7) catalase: positive (8) strictly aerobic Such strain agrees in all tested characteristic with the type strain of *Achromobacter xylosoxydans* DSM 2402, with the exception of hydrolysis of acetamide.

Usually, before the actual reaction, both the culture (cultivation) and the induction of the microorganisms is performed with nicotinic acid. Preferably, the cultivation (culture) and the induction take place with nicotinic acid as the sole carbon, nitrogen and energy source.

Before the addition of substrate (pyrazinecarboxylic acid), the microorganisms then can either be harvested by a usual separating process and resuspended in a fresh medium or the substrate (pyrazinecarboxylic acid) can be added directly to the microorganisms in the initial growth medium. For the actual process then the cell suspension suitably is adjusted to an optical density, at 650 nm, of 1 to 100, preferably of 10 to 30.

As media, those usual among those skilled in the art can be used both for the cultivation and for the actual reaction. Preferably the medium whose composition is given in Table 1 below is used. The substrate (pyrazinecarboxylic acid) can be added once or continuously. Suitably, the substrate addition takes place so that the substrate concentration does not exceed 20 percent by weight, preferably 5 percent by weight. Usually the reaction of pyrazinecarboxylic acid and/or its salts to 5-hydroxypyrazinecarboxylic acid and/or its salts takes place with dormant cells. Suitably the reaction takes place under aerobic conditions at a pH of 4 to 10, preferably at a pH of 6 to 8. The temperature suitably is between 10° and 60° C., preferably between 15° and 45° C. After a usual reaction time of 4 to 100 hours, the product can be precipitated by acidification of the cell-free solution and obtained by working-up methods usual to one skilled in the art. In the case of the sodium salts of 5-hydroxypyrazine-carboxylic acid, the product precipitates already during the reaction.

EXAMPLE 1

*Pseudomonas acidovorans* DSM 4746 was cultivated in a mineral salt medium (Table 1 below) under a continuous addition of sodium nicotinate (0.6 g/l/h) in a fermenter at a pH of 7.0 and at a temperature of 30° C. to an optical density, at 650 nm, of 10. Then the cells were centrifuged off and resuspended in a 2 liter solution, containing 1 mol (146 g) of pyrazinecarboxylic acid-sodium salt, at pH 7.0. The optical density at 650 nm was then 20. After an incubation time of 16 hours under aerobic conditions at pH 7.0 and a temperature of 30° C., no feedstock was able to be detected by UV-spectroscopy. A part of the formed 5-hydroxypyrazinecarboxylic acid-sodium salt crystallized already under these test conditions. The precipitated product was centrifuged off together with the biomass. The formed sediment was then resuspended in 500 ml of water and again centrifuged off. The cell-free supernatants were combined and concentrated by evaporation with a rotary evaporator to 300 ml and cooled to 0° C. The formed crystals were filtered off and dried. Altogether 0.67 mol (108 g) of 5-hydroxypyrazinecarboxylic acid-sodium salt was isolated, corresponding to a yield of 67 percent, relative to the amount of pyrazinecarboxylic acid-sodium salt used.

EXAMPLE 2

*Pseudomonas acidovorans* DSM 4746 was cultivated in a mineral salt medium (Table 1 below) under a continuous addition of sodium nicotinate (0.6 g/l/h) in a fermenter at pH 7.0 and at a temperature of 30° C. to an optical density, at 650 nm, of 10. Then the cells were centrifuged off and resuspended in 100 ml of a solution containing 0.056 mol (7.9 g) of pyrazine-carboxylic acid ammonium salt, pH 7.0. The optical density at 650 nm was then 20. After an incubation time of 24 hours under aerobic conditions at pH 7.0 and a temperature of 30° C., no feedstock was able to be detected by UV-spectroscopy. Then the cell-free supernatant was acidified with concentrated sulfuric acid at pH 2.0 to precipitate 5-hydroxypyrazine-carboxylic acid. Then the suspension was cooled to 4° C. and filtered. The filtration residue was washed twice with 10 ml of water and dried. Altogether 0.054 mol (7.56 g) of 5-hydroxypyrazinecarboxylic acid was able to be isolated, corresponding to a yield of 96 percent, relative to the amount of pyrazinecarboxylic acid-ammonium salt used. The content of 5-hydroxypyrazinecarboxylic by HPLC was >90 percent.

TABLE 1

| Composition of the mineral salt medium | |
|---|---|
| $MgCl_2.6H_2O$ | 0.8 g/l |
| $CaCl_2$ | 0.16 g/l |
| $Na_2SO_4$ | 0.25 g/l |
| $KH_2PO_4$ | 0.4 g/l |
| $Na_2HPO_4$ | 0.9 g/l |
| SLF | 1 ml/l |
| FeEDTA | 15 ml/l |
| Composition of the trace elements (SLF) in the mineral salt medium: | |
| KOH | 15 g/l |
| $EDTANa_2.2H_2O$ | 100 g/l |
| $ZnSO_4.7H_2O$ | 9 g/l |
| $MnCl_2.4H_2O$ | 4 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2$ | 0.18 g/l |
| $Na_2MoO_4.2H_2O$ | 0.2 g/l |
| Composition of FeEDTA: | |
| $EDTANa_2.2H_2O$ | 5 g/l |
| $FeSO_4.7H_2O$ | 2 g/l |
| (The pH of the solution was adjusted to 7.0) | |

What is claimed is:

1. A microbiological process for the production of 5-hydroxypyrazinecarboxylic acid or a salt thereof, comprising (a) converting pyrazinecarboxylic acid or a salt thereof into 5-hydroxypyrazinecarboxylic acid or the salt thereof, by contacting the pyrazinecarboxylic acid or the salt thereof with a microorganism selected from the group consisting of *Pseudomonas acidovorans* DSM 4746, *Pseudomonas putida* NCIB 10521, *Pseudomonas putida* NCIB 8716, *Achromobacter xylosoxydans* DSM 2402, *Achromobacter xylosoxydans* DSM 2783, or a mutant thereof, said mutant maintaining the ability to grow with nicotinic acid and/or at least one of its salts as the sole carbon, nitrogen and energy source, and to convert the pyrazinecarboxylic acid or a salt thereof to the 5-hydroxypyrazinecarboxylic acid or a salt thereof, and (b) accumulating the 5-hydroxypyrazinecarboxylic acid or a salt thereof in the medium in a recoverable amount.

2. The process according to claim 1 wherein the reaction is performed with *Pseudomonas acidovorans* DSM 4746 or a mutant thereof.

3. The process according to claim 1 wherein the reaction is performed with *Pseudomonas putida* NCIB 10521 or a mutant thereof.

4. The process according to claim 1 wherein the reaction is performed with *Pseudomonas putida* NCIB 8176 or a mutant thereof.

5. The process according to claim 1 wherein the reaction is performed with *Achromobacter xylosoxydans* DSM 2402 or a mutant thereof.

6. The process according to claim 1 wherein the reaction is performed with *Achromobacter xylosoxydans* DSM 2783 or a mutant thereof.

7. The process according to claim 1 wherein the reaction takes place under a single or continuous substrate addition, so that the substrate concentration does not exceed 20 percent.

8. The process according to claim 1 wherein the reaction is performed under aerobic conditions at a pH of 4 to 10 and at a temperature of 10° to 60° C.

9. The process according to claim 2 wherein the reaction takes place under a single or continuous substrate addition, so that the substrate concentration does not exceed 20 percent.

10. The process according to claim 3 wherein the reaction takes place under a single or continuous substrate addition, so that the substrate concentration does not exceed 20 percent.

11. The process according to claim 4 wherein the reaction takes place under a single or continuous substrate addition, so that the substrate concentration does not exceed 20 percent.

12. The process according to claim 5 wherein the reaction takes place under a single or continuous substrate addition, so that the substrate concentration does not exceed 20 percent.

13. The process according to claim 6 wherein the reaction takes place under a single or continuous substrate addition, so that the substrate concentration does not exceed 20 percent.

* * * * *